United States Patent [19]

Feinstein

[11] Patent Number: 4,774,958

[45] Date of Patent: * Oct. 4, 1988

[54] ULTRASONIC IMAGING AGENT AND METHOD OF PREPARATION

[76] Inventor: Steven B. Feinstein, 295 Hasting Ave., Highland Park, Ill. 60035

[ * ] Notice: The portion of the term of this patent subsequent to Jan. 12, 2005 has been disclaimed.

[21] Appl. No.: 103,837

[22] Filed: Oct. 1, 1987

Related U.S. Application Data

[63] Continuation-in-part of Ser. No. 805,975, Dec. 5, 1985, Pat. No. 4,718,433, which is a continuation-in-part of Ser. No. 461,664, Jan. 27, 1983, Pat. No. 4,572,203.

[51] Int. Cl.$^4$ ............................................. A61B 10/00
[52] U.S. Cl. .................................. 128/660.01; 424/2; 530/363; 530/427
[58] Field of Search ............................ 128/660; 424/2; 530/363, 427

[56] References Cited

U.S. PATENT DOCUMENTS

| | | | |
|---|---|---|---|
| 4,276,885 | 7/1981 | Tickner et al. | 128/660 |
| 4,466,442 | 8/1984 | Hillmann et al. | 128/653 |
| 4,500,358 | 2/1985 | Mayer et al. | 106/122 |
| 4,548,736 | 10/1985 | Muller et al. | 424/101 |
| 4,572,203 | 2/1986 | Feinstein | 128/661 |
| 4,718,433 | 1/1988 | Feinstein | 128/660 |

OTHER PUBLICATIONS

Feinstein et al. (1984), JACC 3:14–20.
Cate et al. (1984), JACC 3:21–27.
Ophir et al., "US Backscatter from Contrast Producing Collagen Microspheres", U.S. Imag 2 (1980), pp. 67–77.
Bommer et al., Abs., 53rd Scientific Sess., Nov. 17–20 (1980), American Heart Association Meeting.
Bommer et al., Abs., CIRC, Amer. J. Cardiology, vol. 47, 403 (1981).
Tickner, E. G., et al., "Noninvasive Assessment of Pulmonary Hypertension Using the Bubble Ultrasonic Resonance Pressure (BURP) Method", National Technical Information Svc. Dept. #HR-62917-1A, Apr., 1977.

Primary Examiner—Francis J. Jawoski
Attorney, Agent, or Firm—Tilton, Fallon, Lungmus & Chestnut

[57] ABSTRACT

An ultrasonic imaging agent is formed by subjecting an aqueous protein solution to high frequency sonication while heating the solution sufficiently to denature portions of the protein, thereby forming a dispersion of microbubbles stabilized by denatured protein. In a preferred embodiment, the protein solution is formed from human serum albumin, and the formed microbubbles have a relatively uniform size in the 2 to 5 micron range, suitable for imaging of pulmonary or small organ vasculature.

14 Claims, No Drawings

ULTRASONIC IMAGING AGENT AND METHOD OF PREPARATION

RELATED APPLICATIONS

This is a continuation-in-part of co-pending application Ser. No. 805,975, filed Dec. 5, 1985 and now U.S. Pat. No. 4,718,433, which was a continuation-in-part of application Ser. No. 461,664 filed on Jan. 27, 1983, now U.S. Pat. No. 4,572,203.

FIELD OF INVENTION

This invention relates to the field of ultrasonic imaging techniques, and, more specifically, to a medical procedure which utilizes these techniques as a diagnostic tool.

BACKGROUND OF INVENTION

Various technologies exist in which parts of an animal or human body may be imaged so as to aid in diagnosis and therapy. Some of these existing techniques are described in this section.

One of the most well known imaging techniques involves the use of X-rays to visualize skeletal and other internal structures within animals and humans. There are, however, a number of problems associates with the use of X-rays. First, some areas of the body may not be X-rayed safely. In addition, X-rays are dangerous if the amount of exposure is excessive; further, all X-ray radiation absorbed over a lifetime is cumulative. Finally, while X-rays may produce images of the skeletal and other internal structures, X-rays have proved to be relatively unsatisfactory for detailed viewing of certain organ systems and blood vessels.

Another widely used technique is angiography, whereby a radio-opaque dye is injected into an artery. Because the dye highlights the arteries through which it flows, an X-ray may be used to obtain an image of major, large arteries and their significant branches. However, angiography does not permit visualization of under-perfused, ischemic areas of tissue or heart muscle, or the microcirculation. In addition, certain angiographic observations are based upon measurements which may vary depending upon the appparatus used, the placement and angle of lenses, operator skill and similar factors. Moreover, angiography is invasive in that it requires the placement of a catheter into arteries as opposed to veins. Besides requiring hospitalization, angiography may be dangerous.

Another technique, often referred to as radio-nuclide imaging, involves the injection of radioactive substances, such as thallium, into the bloodstream. This technique does not require invasion of the arteries as does angiography, but it does require the use of very expensive and sophisticated machinery. Further, radio-nuclide imaging produces images of only a limited number of view of the heart, and those images may not be of exceptional clarity. Finally, this type of radiation is cumulative over a lifetime and may be dangerous.

Recently, there have been advances in techniques for ultrasonically imaging various parts of the body; these techniques when applied to the heart in particular are known as "echocardiorgraphy". An ultrasonic scanner is used to generate and receive sound waves. The ultrasonic scanner is placed on the body surface overlying the area to be imaged. The sound waves generated by the scanner are directed toward the area to be imaged. The scanner then detects sound waves reflected from the underlying area and translates that data into images.

While such ultrasonic scanners are known in the art, a brief review will be set forth in order to more fully explain the present invention. When ultrasonic energy is transmitted through a substance, the acoustic properties of the substance will depend upon the velocity of the tranmission and the density of the substance. Changes in the substance's acoustic properties (or acoustic impedance) will be most prominent at the interface of different substances (i.e., solids, liquids and gases). As a consequence, then ultrasonic energy is directed through various media, the changes in acoustic properties will change the reflection characteristics, resulting in a more intense sound reflection signal received by the ultrasonic scanner.

Early ultrasonic imaging techniques such as echocardiograms suffered from a lack of clarity. As a result, extensive efforts were undertaken to improve the ultrasonic scanners and related equipment. In addition, beginning in 1968, "contrast" agents were injected into the bloodstream in an effort to obtain clearer or "enhanced" ultrasonic images. The prior art contrast agents were liquids containing microbubbles of gas, which sometimes were claimed to be encapsulated with gelatin (see U.S. Pat. No. 4,276,885) or saccharin and sometimes were produced by mechanically agitating, i.e., handshaking, mixtures of various liquids. Other prior art contrast agents are disclosed in an article by J. Ophir, et al. entitled "Ultrasonic Backscatter from Contrast Produced by Collagen Microspheres" in Ultrasonic Imaging 2 (1980), pp. 67–77.

The contrast agents themselves are intense sound wave reflectors because of the acoustic differences between the liquid and the gas microbubbles dissolved therein; thus, when the contrast agents are injected into and perfuse the microvasculature of tissue, clearer images of such tissue may be produced. However, notwithstanding the use of such contrast agents, the image produced, for example, of the myocardial tissue, is of relatively poor quality, is highly variable and is not quantifiable due to the variable size and persistance associated with prior art microbubbles. Further, the problems of air embolism toxicity have not yet been investigated.

SUMMARY OF THE INVENTION

The present invention is directed to an improvement associated with such prior art contrast agents by which smaller and more uniform microbubbles are produced. A second embodiment is directed to the novel use of specifically defined semisolid contrast agents.

The contrast agents of the present invention are (1) echogenic (i.e., capable of reflecting sound waves); (2) small enough to pass through capillaries so as to perfuse tissue previously inaccessible to the prior art contrast agents injected into a peripheral venous site, thereby producing enhanced images of such tissue and organs and permitting differentiation between well-perfused and poorly-perfused tissue; (3) quantifiably reproducible; and (4) sufficiently stable to be stored for reasonable periods of time prior to use.

The method of the present invention (1) permits the imaging of organ systems which could not be imaged using prior art ultrasonic techniques, and (2) permits clearer, more detailed imaging of certain areas which were viewable using such prior art techniques.

In the preferred embodiment of the present invention, a viscous protein solution (e.g., 5% human serum albumin) is subjected to high frequency (5,000 to 30,000 Hz) ultrasonic energy. As a result, microbubbles having a diameter of approximately 6 to 20 microns are produced. The 5% albumin solution shows the best results in forming small microbubbles, primarily having a diameter in the range of 2-4 microns. For ease of reference such microbubbles will be referred to herein as "sonicated" microbubbles. As described in great detail hereinbelow, such sonicated microbubbles have been found to be improved contrast agents.

The microbubbles or microspheres comprising protein or derivatives thereof in an aqueous solution are formed into stable contrast agents by any of a number of methods known in the art for physically (via heat) or chemically altering the protein or derivatives to denature or fix the material. For example, the use of heat applied to the contrast agent after formation thereof, or during formation as a result of the sonication of the same is one method for denaturing the protein material to form stable contrast agents. As a second method, fixation (i.e., chemical denaturation) of the protein material using formaldehyde or gluteraldehyde may also be utilized to form stable contrast agents.

The contrast agents of the present invention are detected by conventional ultrasonic scanning equipment and translated into images in the manner described above. The use of the microparticles is especially advantageous in that it obviates the need to introduce gaseous bubbles as contrast agents in the human or animal system, and thus eliminates the air embolism toxicity risks inherent in that procedure. Depending upon whether the microparticles are to be used exclusively in animal research or for diagnostic and therapeutic purposes, the potential biocompatability of the particular type of microparticle is a significant consideration.

Thus, while overcoming many of the problems associated with the prior art, the present invention makes possible the production of unique images of various organ systems. Although the invention technique is applicable to various anumal and human body organ systems, its novel features and advantages may be better understood from the following description of its use in obtaining images of myocardial tissue and perfusion or blood flow patterns.

The present invention therefore in addition to providing an improved method of ultrasonic imaging also encompasses a novel method of producing an ultrasonic imaging agent, and the imaging agent. The method of producing the ultrasonic imaging agent comprises, in general, the steps of forming an aqueous protein solution, subjecting said solution to high frequency sonication while heating the solution sufficiently to denature portions of the protein, forming a dispersion of microbubbles of relatively uniform size stabilized by the denatured protein. In preferred embodiments, substantailly all of the resulting microbubbles have diameters less than 9 microns, such as, in optimum embodiments, predominantly in the range from 2 to 5 microns.

DETAILED DESCRIPTION

Ultrasonic scanning equipment consists of a scanner and imaging apparatus. The equipment produces visual images of a predetermined area, in this case, the heart region of a human body. Typically, the scanner is placed directly on the skin over the area to be imaged. The scanner houses various electronic components including ultrasonic transducers. The scanner produces ultrasonic waves which perform a sector scan of the heart region. The ultrasonic waves are reflected by the various portions of the heart region and are received by the generating transducer and processed in accordance with pulse-echo methods known in the art. After processing, signals are sent to the imaging apparatus (also well known in the art) for viewing.

In the method of the present invention, after the patient is "prepped" and the scanner is in place, the sonicated microbubble or microparticle contrast agent is injected, for example, through an arm vein. Continuing the example, the contrast agent flows through a vein to the right venous side of the heart, through the main pulmonary artery leading to the lungs, across the lungs, through the capillaries, into the pulmonary vein, and finally into the left atrium and the left ventricular cavity of the heart.

The present invention is directed to sonicated microbubbles used as contrast agents. It has been found that the use of sonicated microbubbles produces images having vividly contrasting areas. In particular, such microbubbles (1) may be biocompatible or biodegradable, (2) are small enough to pass through the capillary beds which are about 8 to 10 microns in size and (3) have acoustic properties making them echogenic. While not to be bound by any theory, the sonicated microbubbles of the present invention produce noticeably clearer and more detailed images of the myocardial tissue and microvasculature, as compared with prior art contrast agents.

Following a procedure described in my U.S. Pat. No. 4,572,203, microbubbles were produced from a mixture of Renografin-76 (a relatively non-toxic, biocompatible, radio-opaque dye well known in the art) and saline in a one-to-one ratio. This mixture was sonicated, i.e., subjected to high frequency energy, for about 30 seconds by a Heat System 375 watt sonicator. Such sonicators are well known in the art for other uses, and usually emit ultrasonic energy of 20,000 Hertz (Hz), although energies of 5,000 to 30,000 Hz or even higher are within the scope of the present invention.

In the presently preferred embodiment of the invention, a solution of protein or derivatives thereof, capable of forming microbubbles or microspheres when sonicated in accordance with the above-described procedure, is used. One example of a useful solution is a 5% aqueous solution of human serum albumin, referred to herein as albumin. Albumin in solution is commercially available from any of a number of sources. While not being bound by any particular theory of operation, it appears that sonication of the solution under conditions discussed above causes the formation of microbubbles. The resulting microbubbles are substantially different from those prepared from solutions of dextrose, sorbitol, or Renografin in that the walls of the microbubbles themselves are significantly more stable, thereby making the microbubbles themselves more stable. The stability of these microbubbles is believed to be a result of the fact that the sonicator heats the albumin to a temperature sufficient to denature the protein. The sonication can also create bubbles primarily in the range of 2-4 microns. Preferably, substantially all of the microbubbles are in the range of 2-4 microns, as determined by a Coulter Counter, using techniques well known in the art. In an experimental preparation for the microbubbles produced, approximately 8 million per milliliter (ml) of solution were in the 2-4 micron range, approximately 1 million microbubbles per ml in the 4-5 micron range, less an 0.5 million microbubbles per ml in the 5-6 micron range, and relatively negligible amounts of microbubbles in the range above 6 microns were formed. The microbubbles had diameters of less than 9 microns, and the predominant size was in the range from 2 to 5 microns.

As an alternative to heat treatment of the microbubbles as a result of sonication, the protein can be denatured and the microbubbles stabilized by heat treatment to a temperature in the range of 50° to 60° C., with the actual temperature in the range depending on the protein, proteins used, or protein derivatives used. The specific temperature and conditions for denaturation of the various proteins which may be used for the present invention are generally known in the art.

The microbubbles formed from 5% albumin may, in the alternative, be stabilized to form a commercially, clinically usable contrast agent by treatment with various chemical agents which chemically denature, or "fix", the protein, and derivatives thereof. Chemical denaturation of the protein (or derivatives) may be accomplished by either binding the protein with a difunctional aldehyde, such as glyteraldehyde. For the latter procedure of stabilizing the invented microbubble contrast agent, the microbubbles may be reacted with 0.25 grams of 50% aqueous gluteraldehyde per gram of protein at pH 4.5 for 6 hours. The treated contrast agent is then gently and extensively washed to removed as much of the unreacted glyteraldehyde as possible.

The microspheres formed from 5% albumin which have been sonicated as described are stabilized and exist for 48 hours or longer. This may be compared with the above-described sonicated sugar solutions which last a few minutes to a few hours. Thereafter, they are no longer effective contrast agents.

This invented echocontrast agent permits left heart imaging from intravenous injections. The sonicated albumin microbubbles when injected into a peripheral vein are capable of transpulmonary passage. This results in echocardiographic opacification of the left ventricle (LV) cavity as well as myocardial tissue. The sonicated albumin microbubbles are small, stable, and echo reflective targets.

A total of 72 intravenous injections of sonicated albumin microbubbles were performed in 5 dogs. Three to 10 ml of contrast solution, containing a minimum of 500,000 bubbles per ml, were injected into the dorsal forepaw vein in each trial. No significant changes were noted in heart rate, blood pressure or arterial blood gases. LV cavity opacification was graded from 0 (no opacification) to +3 (full LV opacification) with the duration noted in seconds. The overall successful transpulmonary opacification rate was 78% (56/72 trials). LV tissue opacification was always preceded by +3 LV capacity opacification. Successful transpulmonary passage of the sonicated albumin microspheres was observed if (a) the RV contrast opacification was +3 (b) the average sphere size was 4 microns or less, and (c) the sphere concentration was at least one million per milliliter. The results are set forth below in Table 1.

TABLE 1

| LV Cavity Opacification | | Contrast in LV |
|---|---|---|
| Grade | Trials | cavity (seconds) |
| +3 | 11 | 20 ± 8 |
| +2 | 14 | 18 ± 8 |

TABLE 1-continued

| LV Cavity Opacification | | Contrast in LV |
|---|---|---|
| Grade | Trials | cavity (seconds) |
| +1 | 31 | 12 ± 17 |
| 0 | 16 | 0 |

Thus, as shown here, successful opacification of the LV cavity and myocardial tissue is now feasible using peripheral venous injections of sonicated albumin microspheres.

Besides the scanner briefly described above, there exist other ultrasonic scanners, examples of which are disclosed in U.S. Pat. Nos. 4,143,554 and 4,315,435, the disclosures of which are herein incorporated by reference. Basically, these patents relate to various techniques including dynamic crosssectional echography (DCE) for producing sequential two-dimensional images of cross-sectional slices of the animal or human anatomy by means of ultrasound energy at a frame rate sufficient to enable dynamic visualization of moving organs. Types of apparatus utilized in DCE are generally called DCE scanners and transmit and receive short, sonic pulses in the form of narrow beams or lines. The reflected signals' strength is a function of time, which is converted to a position using a nominal sound speed, and is displayed on a cathode ray tube or other suitable devices in a manner somewhat analogous to radar or sonar displays. While DCE can be used to produce images of many organ systems including the liver, gall bladder, pancreas and kidney, it is frequently used for visualization of tissue and major blood vessels of the heart.

Existing DCE scanners can be classified according to the geometry of their field of view (linear or sector scanning), according to the means used for scanning that field of view (mechanical or electronic scanning) and according to whether the transducer scans the patient or object through an intervening water bath or by direct contact with the surface of the object, as, for example, the skin of a patient using an appropriate contact gel or oil. Linear scanners produce a scan of the anatomy consisting of a set of nominally parallel scan lines, displaced with respect to one another by a line spacing roughly comparable to the effective width of each line, as determined primarily by the transducers used in the apparatus. The cross-section imaged by such scanners is therefore approximately rectangular in shape, its width being determined by the line spacing and total number of lines, while its depth is determined by the penetration range of the ultrasound energy into the tissue. Linear scanners are generally used where there is a relatively extended region of the body surface from which access to the parts of interest of the anatomy is possible, such as in the abdominal organs.

Sector scanners produce a scan of the anatomy consisting of a fan of divergent lines spaced angularly from one another, but intersecting (nominally) at a point. The angular spacing is even or uneven, depending upon the apparatus, and is roughly comparable to the effective angular width of each line. Sector scanners are generally used where the anatomical window or region of the body surface from which access to the anatomical part of interest is relatively small, as in the adult heart, the brain, and the eye.

Another type of sector scanner is mechanical in nature and can be further divided into two subclasses, oscillating transducer scanners and rotating transducer scanners. An oscillating transducer scanner is one in which a single transducer is oscillated about an axis nominally line in the front plane and passing through the center of the transducer with an appropriate angle sensor being used to monitor the angular position of the transducer at any time. In a typical rotating transducer scanner, several transducers pin inside a small dome filled with liquid, with one transducer at a time scanning the area of interest. These and other scanners are within the scope of the present invention.

As stated above, in attempting to find a safe, reproducible, quantifiable contrast agent for use in reproducing an enhanced ultrasonic image of the tissue under study, researchers have used saccharin and gelatin encapsulated microbubbles of nitrogen or carbon dioxide gas having a mean size of approximately 75 microns, pressurized gas in liquids (e.g., $H_2O_2$), and mechanically agitated (hand shaken) mixtures of liquid solutions. However, since the pulmonary artery capillaries are about 8 to 10 microns in diameter, the 75 micron encapsulated microbubbles may not cross the capillary bed and, as a result, their use would require a direct injection into the area to be imaged or an arterial injection involving the same risks as the invasive approach of angiography discussed above. Further, microbubbles produced by agitating various liquids other than by sonicating them have wide variability of size. Variable amounts of such non-encapsulated agitated microbubbles can pass through capillaries, but the present state of the art has only produced qualitative data due to the inability to control the variables described above. These contrast agents all work to some degree, but suffer from a number of problems including the fact that the size of the bubbles is not uniform. These and other problems are overcome by the sonicated microbubbles of the present invention.

However, while sonicated microbubbles are more uniform in size and produce enhanced images, the potential problems associated with the introduction of air remain. The danger of injecting microbubbles, encapsulated or not, into the heart is that the bubbles eventually collapse and the amount of dissolved air may be toxic in the arterial system (e.g., of the brain and kidneys) as well as in other microcirculatory systems.

Thus, it is evident that the particular contrast agent selected will depend upon the purpose of the imaging. For example, an agent's potential risk factors should be considered for diagnostic or therapeutic uses. The size of the contrast material is also of concern. If the particles are too large they will not pass through the capillaries and thus will require direct or arterial injections if the area to be imaged lies beyond the capillaries. On the other hand, if the contrast agent is too small, it may not reflect sound waves emitted by the ultrasonic transducer.

The microbubbles may be used for imaging a wide variety of areas, even when injected at a peripheral venous site. Those areas include (without limitation): (1) the venous drainage system to the heart; (2) the myocardial tissue and perfusion characteristics during an exercise treadmill test or the like; and (3) myocardial tissue after an oral ingestion or intravenous injection of drugs designed to increase blood flow to the tissues. Additionally, the microparticles may be useful in delineating changes in the myocardial tissue perfusion due to interventions such as (1) coronary artery vein grafting; (2) coronary artery angioplasty (balloon dilitation of a narrowed artery); (3) use of thrombolytic agents (such as streptokinase) to dissolve clots in coronary arteries; or (4) perfusion defects or changes due to a recent heart attack.

Furthermore, at the time of a coronary angiogram (or a digital subtraction angiogram) an injection of the microparticles may provide data with respect to tissue perfusion characteristics that would augment and complement the data obtained from the angiogram procedure, which identifies only the anatomy of the blood vessels.

Through the use of the microbubbles of the present invention, other noncardiac organ systems including without limitation the liver, spleen, kidney, etc. that are presently imaged by ultrasonic techniques may be susceptible to an enhancement of such currently obtainable images, and/or the generation of new images showing perfusion and flow characteristics that had not previously been susceptible to imaging using prior art ultrasonic imaging techniques.

Having described the invention, it is obvious that other modifications may be made by those skilled in the art. For example, other water-soluble proteins can be used in place of albumin, such as hemoglobin.

I claim:

1. The method of producing an ultrasonic imaging agent, comprising the steps of forming an aqueous protein solution, subjecting said solution to high frequency sonication while heating the solution sufficiently to denature portions of the protein, and forming a dispersion of microbubbles of relatively uniform size stabilized by the denatured protein.

2. The method of claim 1 in which said aqueous protein solution is formed from albumin.

3. The method of claims 1 or 2 in which said stabilized dispersion of microbubbles is formed with substantially all of the microbubbles having diameters less than 9 microns.

4. The method of claim 1 in which said stabilized dispersion of microbubbles is formed with the microbubbles having diameters predominantly in the range from 2 to 5 microns.

5. The method of claim 1 in which said solution is heated sufficiently by means of the sonication to denature said protein portions.

6. The ultrasonic imaging agent produced by the method of claims 1 or 2.

7. The method of producing an ultrasonic imaging agent, comprising the steps of forming an aqueous albumin solution, subjecting said solution to high frequency sonication while heating the solution sufficiently to denature portions of the albumin, and forming a dispersion of microbubbles of relatively uniform size stabilized by the denatured albumin, said microbubbles having diameters predominantly in the range from 2 to 5 microns.

8. The method of claim 7 in which said albumin is human serum albumin.

9. The ultrasonic imaging agent produced by the method of claims 7 or 8.

10. The method of producing an ultrasonic imaging agent, comprising the steps of forming an aqueous protein solution, subjecting said solution to high frequency sonication while heating said solution sufficiently by means of the sonication to denature portions of the protein, said sonication being carried out by applying ultrasonic energy in a range from 5,000 to 30,000 Hertz (Hz), and forming a dispersion of microbubbles in said solution of relatively uniform size stabilized by the denatured protein, substantially all of the microbubbles having diameters of less than 9 microns.

11. The method of claim 10 in which said stabilized dispersion of microbubbles is formed with the microbubbles having diameters predominantly in the range from 2 to 5 microns.

12. The method of claim 10 in which said protein solution is formed from albumin.

13. The method of claim 10 in which said protein solution is formed from human serum albumin, and in which said stabilized microbubbles have diameters predominantly in the range from 2 to 5 microns.

14. The ultrasonic imaging agent produced by the method of claims 10, 11, 12 or 13.

* * * * *